(12) United States Patent
Lam et al.

(10) Patent No.: US 7,291,456 B2
(45) Date of Patent: Nov. 6, 2007

(54) METHOD FOR DETERMINING DIFFERENCES IN MOLECULAR INTERACTIONS AND FOR SCREENING A COMBINATORIAL LIBRARY

(75) Inventors: Kit S. Lam, Davis, CA (US); Alan L. Lehman, Sacramento, CA (US)

(73) Assignee: The Regents of the University of California, Oakland, CA (US)

( * ) Notice: Subject to any disclaimer, the term of this patent is extended or adjusted under 35 U.S.C. 154(b) by 897 days.

(21) Appl. No.: 10/057,178

(22) Filed: Jan. 24, 2002

(65) Prior Publication Data

US 2003/0139322 A1 Jul. 24, 2003

(51) Int. Cl.
*C12Q 1/68* (2006.01)
(52) U.S. Cl. .......................................... 435/6
(58) Field of Classification Search ............... None
See application file for complete search history.

(56) References Cited

U.S. PATENT DOCUMENTS

| | | | |
|---|---|---|---|
| 5,257,182 A | 10/1993 | Luck | |
| 5,510,240 A | 4/1996 | Lam et al. | |
| 5,541,061 A | 7/1996 | Fodor et al. | |
| 5,601,992 A | 2/1997 | Lerner et al. | |
| 5,635,598 A | 6/1997 | Lebl et al. | |
| 5,650,489 A | 7/1997 | Lam et al. | |
| 5,651,943 A | 7/1997 | Lam et al. | |
| 5,827,748 A | 10/1998 | Golden | |
| 5,840,485 A | 11/1998 | Lebl et al. | |
| 5,858,670 A | 1/1999 | Lam et al. | |
| 5,985,836 A | 11/1999 | Bastek et al. | |
| 6,015,561 A | 1/2000 | Alvarez | |
| 6,080,548 A | 6/2000 | Au-Young et al. | |
| 6,090,912 A | 7/2000 | Lebl et al. | |
| 6,183,981 B1 | 2/2001 | Gonzalez-Lima | |
| 6,191,256 B1 | 2/2001 | Chen et al. | |
| 6,194,158 B1 | 2/2001 | Kroes et al. | |
| 6,233,480 B1 | 5/2001 | Hochman et al. | |
| 6,236,747 B1 | 5/2001 | King et al. | |

FOREIGN PATENT DOCUMENTS

| | | | |
|---|---|---|---|
| EP | 0742438 A2 | * | 11/1996 |
| EP | 0742438 A3 | | 11/1996 |
| WO | WO9733169 | | 9/1997 |
| WO | WO9960529 | | 11/1999 |
| WO | WO 01/40265 | * | 6/2001 |
| WO | WO0140265 A2 | | 6/2001 |

OTHER PUBLICATIONS

Lam, K. S.; Wade, S.; Abdul-Latif, F.; Lebl, M. "Application of a dual color detection scheme in the screening of a random combinatorial peptide library" *Journal Immunological Methods* 1995, 180, 219-223.*

Lam, K. S. "Application of combinatorial library methods in cancer research and drug discovery" *Anti-Cancer Drug Design* 1997, 12, 145-167.*

Tizard et al. "DiffScreen: the merging of image subtraction and molecular genetics for the rapid analysis of differentially screened cDNA libraries" *CABIOS* 1994, 10(2), 209-210.*

Lam et al., "Application of a dual color detection scheme in the screening of a random combinatorial peptide library" *Journal of Immunological Methods* 1995, 180, 219-223.*

Tizard, Brett K., Jo-Ann L. Stanton, and Nigel G. Laing. "DiffScreen: the merging of image subtraction and molecular genetics for the rapid analysis of differentially screened cDNA libraries." *Cabios* 10, No. 2 (1994): 209-210.

Liu, Gang, Yemei Fan, James R. Carlson, Zhan-Gong Zhao, and Kit S. Lam. "Solution-Phase Synthesis of a 1,5-Dialkylamino-2,4-dinitrobenzene Library and the Identification of Novel Antibacterial Compounds from This Library." *J. Comb. Chem* 2, No. 5 (Aug. 3, 2000): 467-474.

Lam, Kit S. "Application of combinatorial library methods in cancer research and drug discovery." *Anti-Cancer Drug Design* 12 (1997): 145-167.

Lebl, Michal, Viktor Krchňák, Nikolai F. Sepetov, Bruce Seligmann, Peter Strop, Stephen Felder, and Kit S. Lam. "One-Bead-One-Structure Combinatorial Libraries." *Biopolymers (Peptide Science)* 37 (1995): 177-198.

(Continued)

*Primary Examiner*—Jon D. Epperson
(74) *Attorney, Agent, or Firm*—Audrey A. Millemann; Weintraub Genshlea Chediak

(57) ABSTRACT

The invention includes a method for determining the differences between the molecular interactions of two different mixtures of molecules and identifying ligands specific for molecules in one mixture. The method utilizes a combinatorial library to compare the molecular interactions of the two mixtures and eliminates those interactions that are common to both mixtures and those that are unique to the first mixture, such that interactions essentially unique to the target mixture are identified. Ligands specific for molecules in the target mixture can then be identified. The invention also includes a method of screening a combinatorial library to distinguish between true positive beads and false positive beads and to provide for the identification of ligands specific for target molecules.

2 Claims, 2 Drawing Sheets

OTHER PUBLICATIONS

Lam, Kit S., Sydney E. Salmon, Evan M. Hersh, Victor J. Hruby, Wieslaw M. Kazmierski, and Richard J. Knapp. "A new type of synthetic peptide library for identifying ligand-binding activity." *Nature* 354 (Nov. 7, 1991): 82-84.

Lam, Kit. S. and Michal Lebl. "Selectide Technology: Bead-Binding Screening." *METHODS: A Companion to Methods in Enzymology* 6 (1994): 372-380.

Lam, Kit S., Zhan-Gong Zhao, Shelly Wade, Viktor Krchňák, and Michal Lebl. "Identification of Small Peptides That Interact Specifically With a Small Organic Dye." *Drug Development Research* 33 (1994): 157-160.

Wu, Jinzi, Qingyan N. Ma, and Kit S. Lam. "Identifying Substrate Motifs of Protein Kinases by a Random Library Approach." *Biochemistry* 33 (1994): 14825-14833.

Smith, M. H., A. A. Nuara, J. G. Egen, D. B. Sirjani, K. S. Lam, and W. J. Grives. "Baculoviral expressed HLA class I heavy chains used to screen a synthetic peptide library for Allele-Specific peptide binding motifs." *Molecular Immunology* 35 (1998): 1033-1043.

Pennington, Michael E., Kit S. Lam, and Anne E. Cress. "The use of a combinatorial library method to isolate human tumor cell adhesion peptides." *Molecular Diversity* 2 (1996): 19-28.

Lam, Kit S., Michal Lebl, and Viktor Krchňák. "The 'One-Bead-One-Compound' Combinatorial Library Method." *Chem. Rev.* 97 (1997): 411-448.

Lam, Kit S. Enzyme-Linked Colorimetric Screening of a One-Bead One-Compound Combinatorial Library. *Methods in Molecular Biology* 87: *Combinatorial Peptide Library Protocols* (1998): 7-12.

Aina, Olulanu H., Thomas Sroka, Man-Ling Chen, and Kit S. Lam. Therapeutic Cancer Targeting Peptides. Published online Oct. 7, 2002 in *Wiley InterScience* (www.interscience.wiley.com). DOI 10.1002/bip.10257.

Lam, Kit S. and Michal Lebl. Synthethis and Screening of a "one-Bead-One-Compound" Combinatorial Peptide Library. *Methods in Molecular and Cellular Biology* 6 (1995/1996): 15-25.

* cited by examiner

|  | Image A | Image B | Image C |
|---|---|---|---|
| Bead with no bound molecules | ○ | ○ | |
| False positive bead | ◉ | ◉ | ◎ |
| Bead binds molecule in first mixture | ◉ | ◉ | ◎ |
| Bead binds molecule unique to target mixture | ○ | ◉ | ● |

FIG. 2

METHOD FOR DETERMINING DIFFERENCES IN MOLECULAR INTERACTIONS AND FOR SCREENING A COMBINATORIAL LIBRARY

The United States Government has a paid-up license in this invention and the right in limited circumstances to require the patent owner to license others on reasonable terms as provided for by the terms of Grant Nos. R21 CA78909 and R33 CA86364, awarded by the National Institutes of Health/National Cancer Institute.

BACKGROUND OF THE INVENTION

1. Field of the Invention

The invention relates generally to methods for determining the differences between the molecular interactions of two different mixtures of molecules and identifying ligands specific for molecules of one mixture. The invention also relates to screening methods for one-bead-one-compound combinatorial libraries.

2. Description of Related Art

Combinatorial libraries can be used to study interactions between the molecules of a cell. In particular, the one-bead-one-compound library method (Lam, Kit S. et al. "A new type of synthetic peptide library for identifying ligand-binding activity." Nature 354 (1991): 82-84) has been used to create libraries of compounds such as peptides, chemical oligomers, and small molecules directed against targets such as antibodies, proteases, streptavidin and other enzymes, as well as bacteria and whole cells. The screening of a bead library with a target molecule or target mixture of molecules results in the identification of beads, referred to as true positive beads, that have bound the target molecules. The chemical structures of the compounds on the true positive beads can then be identified and the compounds confirmed as ligands for the target molecules. The ligands can then be used to determine the interactions with, and structures of, the target molecules.

There is a need for a method for comparing, and determining the differences between, the molecular interactions of two different mixtures of molecules, in particular, functionally-related molecules derived from normal cells and cancer cells. There is also a need for a method for determining ligands specific for molecules in one of the two mixtures, referred to as the target mixture.

There is also a need for a method for accurately screening a combinatorial library to determine which solid phase supports are true positives. A problem with most existing screening methods, which include the use of enzymes, radionuclides, fluorescent probes, and color dyes, is that they result in some beads, referred to as false positives, that directly bind chemicals or reagents used in the screening process. This problem is significant where millions of beads are being screened, as there may be only a small number of true positive beads among a larger number of false positive beads. Thus, a screening method is needed that will accurately identify a small number of true positive beads out of a large number of false positive beads.

SUMMARY OF THE INVENTION

The present invention is directed to a quick and efficient method for comparing and determining the differences between the molecular interactions of two different mixtures of molecules and of identifying ligands specific for molecules in one of the mixtures, the target mixture. The method compares the molecular interactions of the two mixtures and eliminates those interactions that are common to both mixtures and those that are unique to the first mixture, such that the interactions essentially unique to the target mixture are identified. Then, ligands specific for molecules in the target mixture can be identified.

The method comprises: preparing first and second mixtures of molecules with a tag or label, where the second mixture is the target mixture; introducing the first mixture to a combinatorial library of solid phase supports; incubating the library with the first mixture of molecules; performing a first marking step to mark the solid phase supports that have molecules of the first mixture bound to them; introducing the target mixture to the library; incubating the library with the target mixture of molecules; immobilizing the library; obtaining a first image, referred to as image "A," before the marking of any solid phase supports that have molecules of the target mixture bound to them, showing as marked only those solid phase supports that were marked in the first marking step; performing a second marking step to mark the solid phase supports that have molecules of the target mixture bound to them; obtaining a second image, referred to as image "B," showing as marked those solid phase supports that were marked in the first marking step and those that were marked in the second marking step; performing image analysis on the first and second images to create a third image referred to as "C," showing, for each solid phase support, (B−A)/A, such that image "C" identifies the solid phase supports that were marked only in the second marking step; isolating a solid phase support identified in image "C"; and determining the chemical structure of the compound on that solid phase support.

The invention is also directed to a method for screening a combinatorial bead library that quickly and accurately distinguishes between a small number of true positive beads and a large number of false positive beads and provides for the identification of ligands specific for a target molecule.

BRIEF DESCRIPTION OF THE DRAWINGS

FIG. 1 is a diagram showing an example of images "A," "B," and "C" of the method of the first embodiment of the invention.

FIG. 2 is a table comparing the appearance of beads shown in images "A," "B," and "C."

DETAILED DESCRIPTION OF THE PREFERRED EMBODIMENTS

Figure 1A:
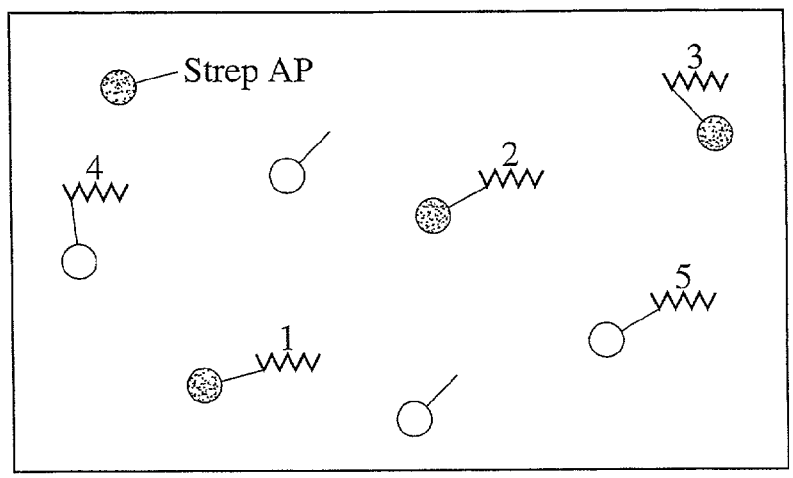
FIG. 1A depicts an example of image "A," showing as stained the beads marked in the first marking step after screening with the first mixture of molecules.

Method for Determining Differences between Molecular Interactions of Two Different Mixtures of Molecules The first embodiment of the invention is a method for determining the differences between the molecular interactions of two different mixtures of molecules and of identifying ligands specific for molecules in one of the two mixtures, the target mixture. The method is not limited to mixtures of molecules and can be used to determine the differences between the molecular interactions of two different molecules (e.g. two different forms of a molecule) and to identify ligands specific for one form of the molecule. For purposes of this description, the phrase "mixture of molecules" shall be understood to mean a single type of molecule or a mixture of molecule types.

The mixtures to be compared are preferably functionally related mixtures of molecules, for example, protein extracts from normal cells and cancer cells of the same tissue or organ, from different stages in the cell cycle, from wild type and mutant organisms, or from wild type and mutant proteins, or plasma and serum.

The method includes the following steps. A one-bead-one-compound combinatorial library is synthesized, preferably by the "split synthesis" method. Lam et al., "A new type of synthetic peptide library," 82-84. The library may consist of peptides, chemical oligomers, oligonucleotides, or other small molecules. For example, a peptide library containing cXXXXXc peptides, where "X" is any L-amino acid, excluding cysteine, arginine, and lysine, and "c" is D-cysteine, can be used. A solid phase support, such as beads or discs made of polystyrene, agarose, acrylamide, glass, plastic, or paramagnetic substances, is used. For purposes of this description, the term "beads" shall be understood to mean any type of solid phase support. For a peptide library, a standard synthetic solid phase peptide synthesis method, such as fluorenylmethyoxycarbonyl (Fmoc) chemistry or t-butyloxycarbonyl (Boc) chemistry, is used.

The first mixture of molecules and the second mixture of molecules (the target mixture) are tagged or labeled in a fashion that will allow for subsequent identification of positive beads. Various types of tagging systems can be used, such as biotinylation where biotin is the label and streptavidin-alkaline phosphatase conjugate is the label binder, flag antigen and antiflag antibody, antigen and corresponding antibody, glutathione-S-transferase and glutathione alkaline phosphatase conjugate, or other systems known to those skilled in the art. Enzyme reporting systems other than alkaline phosphatase may be used, such as horseradish peroxidase and glucose oxidase. The tagging is performed according to standard methods pertaining to the system that is used.

Unless otherwise indicated, the screening of the beads and the bead reactions and incubations are performed in a reaction vessel, preferably a column, although a test tube or other container can be used. The number of beads is preferably about 100,000 to 1,000,000, although the method will work for a smaller or greater number of beads. The size of the column depends on the size and number of beads used. Columns from about 1 ml to 10 ml in size are appropriate for about 100,000 to 1,000,000 beads of about 80 microns in diameter, respectively. The level of solution in the column or other vessel is maintained above the level of the beads, so that the beads do not become dry. All of the bead reactions are incubated at about room temperature, preferably keeping the beads in motion. All of the bead reactions are incubated, and the beads are washed, in a solution that is suitable for the target mixture. Such solutions may include HEPES, Tris, and phosphate-based buffers, such as PBS.

The beads are pretreated with a solution of a blocking agent in buffer to block non-specific binding. Suitable blocking agents include gelatin and bovine serum albumin, for example.

The beads are screened with the first mixture of molecules by incubating the beads with a solution of the first mixture of molecules. The amount of the first mixture should be sufficient to saturate potential binding sites on the beads. The incubation period should be sufficient for the molecules of the first mixture to bind to the beads, and is typically about one hour. An incubation period of more or less than an hour may be used; however, an incubation period that is too long may result in degradation of the proteins or other molecules in the mixture, while an incubation period that is too short may result in insufficient time for the molecules to bind to the beads.

After the incubation period, the beads are washed to remove unbound or loosely associated proteins or other molecules.

If the tagging system utilizes a label and a label binder, then, before the first marking step is performed, the beads are incubated with a solution of the label binder for about one hour. If, for example, the label is biotin, then the label binder is a streptavidin-alkaline phosphatase conjugate in buffer. After the incubation period, the beads are first washed to remove any unbound label binder, for example, streptavidin-alkaline phosphatase conjugate, and then washed in a solution suitable for the tagging system used. If the tagging system does not utilize a label and a label binder, then the first marking step follows directly.

The next step is the first marking step. The purpose of this step is to mark the beads that have molecules of the first mixture bound to them. Marking agents include an enzyme substrate, such as 5-bromo-4-chloro-3-indolyl-phosphate (BCIP) for alkaline phosphatase, and radioactive, color, or fluorescent compounds. The beads are marked by incubating them in a solution of the marking agent, such as BCIP in alkaline phosphatase buffer, for about one hour. A longer incubation period, such as overnight, may be used if there are small amounts of molecules bound to the beads. This incubation results in the marking of the beads that have molecules of the first mixture, or chemicals or reagents used in the preceding steps, such as streptavidin-alkaline phosphatase conjugate, bound to them, leaving the beads with no bound molecules unmarked. If BCIP was used as the marking agent, the marked beads will now be stained blue because, in the presence of alkaline phosphatase, BCIP is converted to indigo which appears blue and precipitates as an insoluble marker on the beads that have proteins or other molecules bound to them. The unmarked beads will remain colorless.

After the incubation period, the beads are washed to remove any unreacted marking agent.

The beads that are now marked, or stained blue if BCIP was used as the marking agent, consist of beads that bound molecules present in the first mixture and false positive beads. The former category may include beads that bound molecules essentially unique to the first mixture and beads that bound molecules common to both the first mixture and the target mixture. In addition to beads, there may be artifacts or contaminants that are marked, such as dust or impurities.

The beads are then screened with the target mixture of molecules. The target mixture has been tagged or labeled in the same fashion as the first mixture of molecules, for example, by biotinylation. The beads are incubated with a solution of the target mixture. The amount of the target mixture is preferably an amount sufficient to saturate potential binding sites on the beads. The incubation period is, for example, about one hour, or longer, preferably about the same time period as was used for the incubation of the beads with the first mixture.

After the incubation period, the beads are washed to remove unbound or loosely associated proteins or other molecules.

If the tagging system utilizes a label and a label binder, then the beads are incubated with a solution of the label binder, for example, streptavidin-alkaline phosphatase conjugate (1.5 mg/ml) in buffer if the label is biotin, diluted between about 1:1000 and 1:100,000, for about one hour. After the incubation period, the beads are first washed to remove any unbound label binder, for example streptavidin-alkaline phosphatase conjugate, and then washed in a solution suitable for the tagging system used. If alkaline phosphatase and BCIP are being used, the buffer is preferably alkaline phosphatase buffer.

If the marking agent that is being used is a substrate that will turn color, such as BCIP, then, after washing, a number of permanently colored beads may be added to the bead mixture to serve as reference points in subsequent steps. The reference beads should be of a color different from that of the color product. If BCIP, which marks the beads by causing them to turn blue, is being used, then red reference beads work well. About one reference bead should be added for every 500 beads of the library.

The beads are immobilized by adding a solution of a suitable support matrix to the beads. The support matrix should be porous enough to allow diffusion of the marking agent. If BCIP is being used, agarose or acrylamide can be used as the support matrix. The solution should be one that is appropriate for the tagging system used; if alkaline phosphatase and BCIP are being used, the buffer is preferably alkaline phosphatase buffer.

The bead-matrix solution is distributed on a surface that permits imaging, such as a thin tray or dish on a flatbed scanner, and allowed to gel. The beads should now be immobilized. A solution appropriate for the tagging system, such as alkaline phosphatase buffer if alkaline phosphatase and BCIP are being used, without the marking agent, is then added to the tray and incubated for enough time to allow the support matrix to reach an equilibrium of size, as the matrix may pull away from the edges of the tray upon addition of the solution. This may take about five minutes. The solution is then removed.

The tray or dish is prepared for imaging to record the position and color intensity of the beads. If the marking agent being used is a substrate that will turn color, then the imaging is preferably accomplished using a flatbed scanner. The tray is placed on the flatbed scanner and prepared for transparency scanning at about 600 to 2400 dpi, preferably at least 1200 dpi, with no sharpening or color adjustments.

Next, the second marking step is begun. The marking agent is added to the immobilized beads in order to mark the beads that have molecules of the target mixture bound to them. The marking agent is preferably the same one that was used in the first marking step. A solution of the marking agent in an appropriate buffer, such as BCIP in alkaline phosphatase buffer, is gently added to the tray on top of the support matrix. The tray is then immediately scanned, before the marking agent has time to react with the tagging system. The resulting graphical image, designated "A," is saved. The purpose of this step is to obtain an image that shows as marked or stained only the beads that were marked in the first marking step after screening with the first mixture: the false positive beads and the beads that bound molecules present in the first mixture. (Unmarked beads will also appear in image "A," but they will be colorless.) If the scanning is not done quickly enough and the marking agent reacts with the tagging system, then some of the beads that have molecules of the target mixture bound to them may also be shown on image "A," and the resulting image analysis will not be as accurate.

Figure 1B:
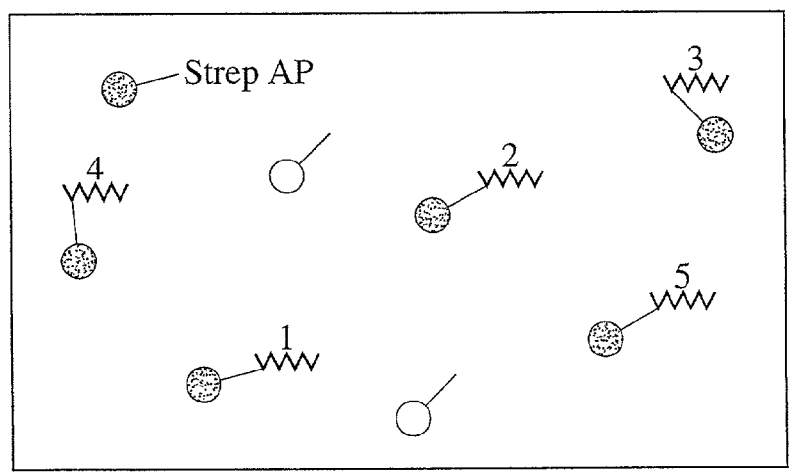
FIG. 1B depicts an example of image "B," showing the beads of FIG. 1A, showing as stained the beads marked in the first marking step after screening with the first mixture of molecules and the beads marked in the second marking step after screening with the target mixture of molecules.
Figure 1C:
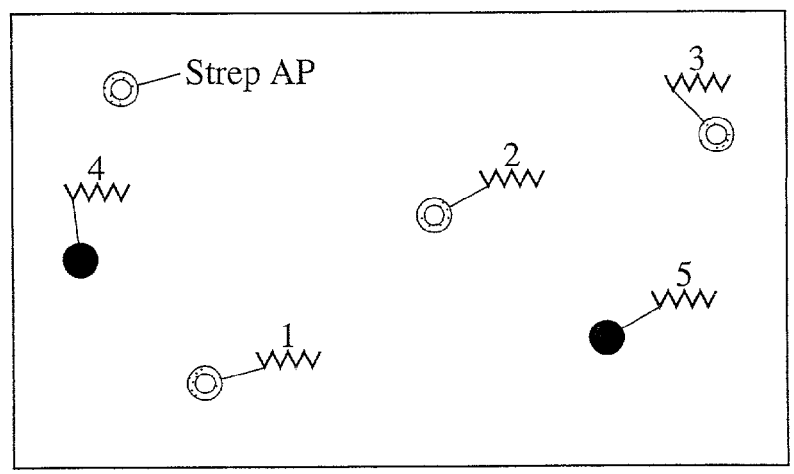
FIG. 1C depicts image "C," created by the application of the formula (B−A)/A to each pair of corresponding pixels present in images "A" and "B" of FIGS. 1A and 1B, respectively.

FIG. 1 shows examples of images "A," "B," and "C" in FIGS. 1A, 1B, and 1C, respectively. In each of FIGS. 1A, 1B, and 1C, the beads are indicated by circles and are shown as if they were immobilized in a support matrix. Each bead has multiple copies of the same compound, indicated by the straight line projecting from the circle. In each of FIGS. 1A, 1B, and 1C, one of the beads has bound a reagent used in the screening process, streptavidin-alkaline phosphatase conjugate, shown as "Strep AP." Other beads are shown with bound proteins, indicated by zigzag lines with a different number for each different protein.

FIG. 1A shows an example of image "A" for eight beads. In this example, the first mixture of molecules contains proteins 1, 2, and 3, and the target mixture contains proteins 3, 4, and 5. Four beads are stained (shown as shaded) after the first marking step: one false positive bead with streptavidin-alkaline phosphatase conjugate bound to it and three beads with proteins 1, 2, or 3 bound to them. Four beads are unstained (shown as unshaded): two beads that have not bound any molecules and two beads that have bound proteins unique to the target mixture (proteins 4 or 5).

The scanning step is preferably performed after the addition of the marking agent, rather than before, in order to minimize any changes that may occur due to the addition of the marking agent, including size changes in the support matrix, slight changes in the position of the tray on the scanner, and changes in the refractive index of the solution in and on the matrix. This will enhance the ability to correctly align the images in later steps. Alternatively, the scanning step may be performed before the addition of the marking agent, but corrections for size and refractive changes would need to be made.

After image "A" is obtained, the second marking step is completed by incubating the immobilized beads for sufficient time to allow the marking agent to react with the tagging system to mark the beads that have molecules of the target mixture bound to them. The tray is periodically rescanned every hour or so, as needed, to ensure that there is sufficient time for the beads with bound molecules to become marked. If BCIP was used as the marking agent, the marked beads will now be stained blue. The unmarked beads will remain colorless.

One of the images is saved and designated "B," preferably an image that shows sufficient differences in intensity of the beads shown as marked in image "A." Image "B" shows as marked or stained the beads that were marked in the first marking step after screening with the first mixture, which, if BCIP was used, may now appear a darker blue, and the beads that were marked in the second marking step which were colorless after screening with the first mixture but became stained after screening with the target mixture. It is the latter category of beads that have bound molecules essentially unique to the target mixture, and it is the molecular interactions between these beads and the molecules bound to them that are essentially unique to the target mixture. (Unmarked beads will also appear in image "B," but they will be colorless.)

FIG. 1B shows image "B" for the eight beads shown in FIG. 1A. Six of the beads are stained (shown as shaded) after the second marking step: the four beads that were stained in FIG. 1A and the two beads that have bound proteins unique to the target mixture (proteins 4 or 5). Two of the beads are unstained (shown as unshaded): the two beads that have not bound any molecules.

The reaction of the marking agent with the tagging system is then stopped. If the marking agent is BCIP, a solution of acid is added to the tray, with gentle shaking, to lower the pH and stop the alkaline phosphatase reaction. The scanned trays can be stored covered, in a humid environment, until needed. Distilled water can be added to prevent dehydration of the support matrix.

Graphical image analysis is performed to compare images "A" and "B." The images are preferably of the same size and are aligned at all common points. If colored reference beads were added earlier, they may now be used to assist in aligning images "A" and "B" so that the two images can be precisely overlaid. Image manipulation, including alignment and conversion to gray scale if desired, is accomplished by the use of software such as Adobe Photoshop.

The comparison of images "A" and "B" is accomplished by applying the formula (B−A)/A to each pair of corresponding points or pixels present in images "A" and "B." Errors due to division by zero are eliminated by adding one where necessary. The numerical results of (B−A)/A are used to create a third image, designated "C," shown in FIG. 1C. This data analysis is performed through the use of custom programming.

Image "C" shows the beads that were marked in image "B" that were not marked in image "A." These are the true positive beads—those that bound molecules essentially unique to the target mixture. Thus, the effect of the application of the formula (B−A)/A is to compare the molecular interactions of the first mixture to those of the target mixture, eliminate those interactions common to both mixtures and those interactions unique to the first mixture, and identify the interactions essentially unique to the target mixture.

In FIG. 1C, the two true positive beads are shown as solid dark circles and have bound proteins 4 or 5 that are unique to the target mixture. Image "C" may also show the beads that were marked in image "A" and also marked in image "B"—those beads that bound molecules present in the first mixture and the false positive beads—but they are distinguishable from the true positive beads. If BCIP was used, these beads appear as doughnuts with a clear inside area and a dark outside ring. In FIG. 1C, these beads are shown as shaded rings. (Image "C" will not show the beads that were not marked in either image "A" or image "B.") The application of (B−A)/A emphasizes the true positive beads by giving substantially more weight to beads that were not marked in image "A" but marked in image "B." Less weight is given to beads that were marked in image "A" and also marked in image "B."

FIG. 2 is a table comparing the appearance of the beads in FIGS. 1A, 1B, and 1C. A bead with no bound molecules appears colorless in both images "A" and "B" and does not appear at all in image "C." A false positive bead, such as a bead that has bound streptavidin-alkaline phosphatase conjugate, appears stained in images "A" and "B" and as a doughnut-shaped ring in image "C." A bead that has bound a molecule present in the first mixture (which may be either unique to the first mixture or also present in the target mixture) appears stained in images "A" and "B" and as a doughnut-shaped ring in image "C." A bead that has bound a molecule unique to the target mixture appears colorless in image "A," stained in image "B," and as a dark circle in image "C."

Image "C" is annotated (for example, with arrows) to indicate the true positive beads of interest. This annotated image "C" can then be used, by overlaying it on image "B," to create a picking template to remove the true positive beads from the support matrix. The tray with the bead support matrix is placed on top of the picking template, and the beads of interest are removed using a pipette tip.

After being removed from the matrix, the true positive beads are stringently washed to separate the beads from the target molecules bound to the beads.

The chemical structure of the compound or ligand on each true positive bead is then determined. In the case of a peptide library, the amino acid sequence can be determined with an automated peptide sequencer.

Method for Screening Combinatorial Bead Library

The second embodiment of the invention is a method of screening a one-bead-one-compound combinatorial library to distinguish between true positive beads and false positive beads and to provide for the identification of ligands specific for a target molecule.

The method includes the following steps. A one-bead-one-compound combinatorial library is synthesized, preferably by the "split synthesis" method. Lam et al., "A new type of synthetic peptide library," 82-84. The library may consist of peptides, chemical oligomers, oligonucleotides, or other small molecules. For example, a peptide library containing cXXXXXc peptides, where "X" is any L-amino acid, excluding cysteine, arginine, and lysine, and "c" is D-cysteine, can be used. A solid phase support, such as beads or discs made of polystyrene, agarose, acrylamide, glass, plastic, or paramagnetic substances, is used. For purposes of this description, the term "beads" shall be understood to mean any type of solid phase support. For a peptide library, a standard synthetic solid phase peptide synthesis method, such as fluorenylmethyoxycarbonyl (Fmoc) chemistry or t-butyloxycarbonyl (Boc) chemistry, is used.

The target molecule or mixture of molecules is tagged or labeled in a fashion that will allow for subsequent identification of positive beads. Various types of tagging systems can be used, such as biotinylation where biotin is the label and streptavidin-alkaline phosphatase conjugate is the label binder, flag antigen and antiflag antibody, antigen and corresponding antibody, glutathione-S-transferase, and glutathione alkaline phosphatase conjugate, or other systems known to those skilled in the art. Enzyme reporting systems other than alkaline phosphatase may be used, such as horseradish peroxidase and glucose oxidase. The tagging is performed according to standard methods pertaining to the system that is used.

Unless otherwise indicated, the screening of the beads and the bead reactions and incubations are performed in a reaction vessel, preferably a column, although a test tube or other container can be used. The number of beads is preferably about 100,000 to 1,000,000, although the method will work for a smaller or greater number of beads. The size of the column depends on the size and number of beads used. Columns from about 1 ml to 10 ml in size are appropriate for about 100,000 to 1,000,000 beads of about 80 microns in diameter, respectively. The level of solution in the column or other vessel is maintained above the level of the beads, so that the beads do not become dry. All of the bead reactions are incubated at about room temperature, preferably keeping the beads in motion. All of the bead reactions are incubated, and the beads are washed, in a solution that is suitable for the target mixture. Such solutions may include HEPES, Tris, and phosphate-based buffers, such as PBS.

The beads are pretreated with a solution of a blocking agent in buffer to block non-specific binding. Suitable blocking agents include gelatin and bovine serum albumin, for example.

If the tagging system utilizes a label and a label binder, then, before the first marking step is performed, the beads are incubated with a solution of the label binder for about one hour. If, for example, the label is biotin, then the label binder is a streptavidin-alkaline phosphatase conjugate in buffer. After the incubation period, the beads are first washed to remove any unbound label binder, for example, streptavidin-alkaline phosphatase conjugate, and then washed in a solution suitable for the tagging system used. If the tagging system does not utilize a label and a label binder, then the first marking step follows directly.

The next step is the first marking step. The purpose of this step is to mark the beads that have reagents, such as the label binder, or chemicals from the reaction, bound to them. Marking agents include an enzyme substrate, such as BCIP for alkaline phosphatase, and radioactive, color, or fluorescent compounds. The beads are marked by incubating them in a solution of the marking agent, such as BCIP in alkaline phosphatase buffer, for about one hour. A longer incubation period, such as overnight, may be used if necessary. This incubation results in the marking of the beads that have chemicals or reagents used in the preceding steps, such as streptavidin-alkaline phosphatase conjugate, bound to them, leaving the beads with no bound molecules unmarked. If BCIP was used as the marking agent, the marked beads will now be stained blue because, in the presence of alkaline phosphatase, BCIP is converted to indigo which appears blue and precipitates as an insoluble marker on the beads that have proteins or other molecules bound to them. The unmarked beads will remain colorless.

After the incubation period, the beads are washed to remove any unreacted marking agent.

The beads that are now marked, or stained blue if BCIP was used as the marking agent, consist of false positive beads. In addition to beads, there may be artifacts or contaminants that are marked, such as dust or impurities.

The beads are then screened with the target molecule or mixture of molecules. The target mixture has been tagged or labeled in a manner compatible with the chemicals and reagents used previously, for example, by biotinylation. The beads are incubated with a solution of the target mixture. The amount of the target mixture is preferably an amount sufficient to saturate potential binding sites on the beads. The incubation period is preferably about one hour.

After the incubation period, the beads are washed to remove unbound or loosely associated proteins or other molecules.

If the tagging system utilizes a label and a label binder, then the beads are incubated with a solution of the label binder, for example, streptavidin-alkaline phosphatase conjugate (1.5 mg/ml) in buffer if the label is biotin, diluted between about 1:1000 and 1:100,000, for about one hour. After the incubation period, the beads are first washed to remove any unbound label binder, for example streptavidin-alkaline phosphatase conjugate, and then washed in a solution suitable for the tagging system used. If alkaline phosphatase and BCIP are being used, the buffer is preferably alkaline phosphatase buffer.

If the marking agent that is being used is a substrate that will turn color, such as BCIP, then, after washing, a number of permanently colored beads may be added to the bead mixture to serve as reference points in subsequent steps. The reference beads should be of a color different from that of the color product. If BCIP, which marks the beads by causing them to turn blue, is being used, then red reference beads work well. About one reference bead should be added for every 500 beads of the library.

The beads are immobilized by adding a solution of a suitable support matrix to the beads. The support matrix should be porous enough to allow diffusion of the marking agent. If BCIP is being used, agarose or acrylamide can be used as the support matrix. The solution should be one that is appropriate for the tagging system used; if alkaline phosphatase and BCIP are being used, the buffer is preferably alkaline phosphatase buffer.

The bead-matrix solution is distributed on a surface that permits imaging, such as a thin tray or dish on a flatbed scanner, and allowed to gel. The beads should now be immobilized. A solution appropriate for the tagging system, such as alkaline phosphatase buffer if alkaline phosphatase and BCIP are being used, without marking agent, is then added to the tray and incubated for enough time to allow the support matrix to reach an equilibrium of size, as the matrix may pull away from the edges of the tray upon addition of the solution. This may take about five minutes. The solution is then removed.

The tray or dish is prepared for imaging to record the position and color intensity of the beads. If the marking agent being used is a substrate that will turn color, then the imaging is preferably accomplished using a flatbed scanner. The tray is placed on the flatbed scanner and prepared for transparency scanning at about 600 to 2400 dpi, preferably at least 1200 dpi, with no sharpening or color adjustments.

Next, the second marking step is begun. The marking agent is added to the immobilized beads in order to mark the beads that have the target molecule or molecules of the target mixture bound to them. The marking agent is preferably the same one that was used in the first marking step. A solution of the marking agent in an appropriate buffer, such as BCIP in alkaline phosphatase buffer, is gently added to the tray on top of the support matrix. The tray is then immediately scanned, before the marking agent has time to react with the tagging system. The resulting graphical image, designated "A," is saved. The purpose of this step is to obtain an image that shows as marked or stained only the beads that were marked in the first marking step after screening with the chemicals and reagents: the false positive beads. (Unmarked beads will also appear in image "A," but they will be colorless.) If the scanning is not done quickly enough and the marking agent reacts with the tagging system, then some of the beads that have molecules of the target mixture bound to them (i.e. the true positive beads) may also be shown on image "A," and the resulting image analysis will not be as accurate.

The scanning step is preferably performed after the addition of the marking agent, rather than before, in order to minimize any changes that may occur due to the addition of the marking agent, including size changes in the support matrix, slight changes in the position of the tray on the scanner, and changes in the refractive index of the solution in and on the matrix. This will enhance the ability to correctly align the images in later steps. Alternatively, the scanning step may be performed before the addition of the marking agent, but corrections for size and refractive changes would need to be made.

After image "A" is obtained, the second marking step is completed by incubating the immobilized beads for sufficient time to allow the marking agent to react with the tagging system to mark the beads that have the target molecule or molecules of the target mixture bound to them.

The tray is periodically rescanned every hour or so, as needed, to ensure that there is sufficient time for the beads with bound molecules to become marked. If BCIP was used as the marking agent, the marked beads will now be stained blue. The unmarked beads will remain colorless.

One of the images is saved and designated "B," preferably an image that shows sufficient differences in intensity of the beads shown as marked in image "A." Image "B" shows as marked or stained the beads that were marked in the first marking step after screening with the chemicals and reagents, which, if BCIP was used, may now appear a darker blue, and the beads that were marked in the second marking step which were colorless after screening with the chemicals and reagents but became stained after screening with the target mixture. It is the latter category of beads that have bound molecules present in the target mixture. (Unmarked beads will also appear in image "B," but they will be colorless.)

The reaction of the marking agent with the tagging system is then stopped. If the marking agent is BCIP, a solution of acid is added to the tray, with gentle shaking, to lower the pH and stop the alkaline phosphatase reaction. The scanned trays can be stored covered, in a humid environment, until needed. Distilled water can be added to prevent dehydration of the support matrix.

Graphical image analysis is performed to compare images "A" and "B." The images are preferably of the same size and are aligned at all common points. If colored reference beads were added earlier, they may now be used to assist in aligning images "A" and "B" so that the two images can be precisely overlaid. Image manipulation, including alignment and conversion to gray scale if desired, is accomplished by the use of software such as Adobe Photoshop.

The comparison of images "A" and "B" is accomplished by applying the formula (B−A)/A to each pair of corresponding points or pixels present in images "A" and "B." Errors due to division by zero are eliminated by adding one where necessary. The numerical results of (B−A)/A are used to create a third image, designated "C." This data analysis is performed through the use of custom programming.

Image "C" shows the beads that were marked in image "B" that were not marked in image "A." These are the true positive beads—those that bound molecules present in the target mixture. Image "C" may also show the beads that were marked in image "A" and also marked in image "B"—the false positive beads—but they are distinguishable from the true positive beads. If BCIP was used, these beads appear as doughnuts with a clear inside area and a dark outside ring. (Image "C" will not show the beads that were not marked in either image "A" or image "B.") The application of (B−A)/A emphasizes the true positive beads by giving substantially more weight to beads that were not marked in image "A" but marked in image "B." Less weight is given to beads that were marked in image "A" and also marked in image "B."

Image "C" is annotated (for example, with arrows) to indicate the true positive beads of interest. This annotated image "C" can then be used, by overlaying it on image "B," to create a picking template to remove the true positive beads from the support matrix. The tray with the bead support matrix is placed on top of the picking template, and the beads of interest are removed using a pipette tip.

After being removed from the matrix, the true positive beads are stringently washed to separate the beads from the target molecules bound to the beads.

The chemical structure of the compound or ligand on each true positive bead is then determined. In the case of a peptide library, the amino acid sequence can be determined with an automated peptide sequencer.

EXAMPLE

The following is an example of the first embodiment of the invention.

General Method. The two mixtures of molecules to be compared were human plasma, referred to as "the target mixture," and human serum, referred to as "the first mixture." Both the plasma and serum were biotinylated with EZ-Link™ Sulfo-NHS-LC-Biotin from Pierce. Bead libraries were generated on TenteGel from Rapp Polymere. Amino acids used in bead library synthesis were from Synpep. Bead library screenings were done in disposable polypropylene columns from Perkin Elmer Life Sciences. All buffer reagents were from Sigma unless otherwise noted. PBS, TBS and BCIP buffers were as described in Lam, Kit S. and Michal Lebl, "Synthesis of a one-bead one-compound combinatorial peptide library," *Methods in Molecular Biology*, vol. 87, *Combinatorial Peptide Library Protocols*. Edited by Shmuel Cabilly (Humana Press: 1997), 1-6. Bead staining utilized BCIP from Bio Synth AG which was hydrolyzed with streptavidin-alkaline phosphatase conjugate from Zymed. Bead immobilization was done in Sea-Plaque agarose from Bio Wittaker Molecular Applications in Omni tray lids from Nunc/Nalgene. Scanned images were generated on a flatbed transparency scanner from Umax. Computer imaging was accomplished with Adobe Photoshop and compiler software was from Metrowerks. Amino acid sequencing was done on an Applied Biosystems Procise 494 Protein Sequencer.

Library Synthesis. "One-bead-one-compound" cXXXXXc peptide libraries were synthesized essentially as described (Lam and Lebl, *Methods in Molecular Biology*, vol. 87) using the "split synthesis approach," where "X" denotes any L-amino acid except for cysteine, arginine, and lysine, and "c" is D-cysteine. TenteGel was used as a solid support and standard Fmoc chemistry was used for the solid phase peptide synthesis reactions. (Stewart and Young 1984. *Solid-Phase Peptide Synthesis*. Pierce Chemical Co. Atherton, E. and R. C. Sheppard. 1989. *Solid Phase Peptide Synthesis: A Practical Approach*. Practical Approach Series.)

Extract Preparation and Biotinlation. Human plasma and serum were prepared by the collection of human blood into stoppered vacuum tubes in the presence of Na-heparin as an anti-coagulant for plasma and in the absence of Na-heparin for serum. Blood was allowed to clot in the tubes for 25 minutes after which the top layer of plasma was collected. Na-heparin was added to the serum to equalize the amount of Na-heparin in plasma and serum after which both samples were centrifuged at 1000 rpm for 20 minutes in a Sorvall SS34 centrifuge rotor. After centrifugation, samples were aliquoted, dialyzed against PBS for four hours at 4° C., quantitated and stored frozen at −80° C. The concentrations of the plasma and serum protein extracts after dialysis were 66.5 and 57.8 mg/ml, respectively.

Plasma and serum were tagged using biotinylation where biotin was the label and streptavidin alkaline phosphatase conjugate was the label binder. Biotinylation was performed according to the manufacturer's instructions. About 0.2 mg of protein was incubated in PBS with a 20-fold molar excess of sulfo-NHS-LC-biotin for 30 minutes at 23° C. The reaction was quenched by the addition of Tris-HCl pH 7.9 to 100 mM. For calculations of molarity, the average molecular weight of the proteins in the plasma and serum solutions was assumed to be 50 kD.

Library Screening. Four experiments were conducted. On average, 250,000 "one-bead-one-compound" beads were screened in each experiment. All bead reactions were performed in 1.5 ml polypropylene disposable micro-columns with inside dimensions of 37 mm×6 mm. Unless otherwise noted, all bead reactions were incubated on a Lab quake bench top rotator (Barnstead/Thermolyne) for 1 hour at 23° C. Bead libraries were stored in PBS with 0.05% sodium-azide. All incubation buffers and components were thoroughly mixed before addition to the column containing the bead library.

The beads were pretreated by placing 250,000 beads in a 1.5 ml column and blocking non-specific protein binding in PBS+0.1% Tween-20, 0.1% gelatin (Sigma) and 0.05% sodium-azide (PBSTGNaN$_3$) for one hour. Following the preblock, the beads were washed three times by the addition of 1.5 ml of PBSTGNaN$_3$, followed by vacuum assisted removal of the wash buffer. The level of the buffer solution in the column was maintained above the level of the beads at all times. At no time were the beads allowed to become dry.

After preblocking, the beads were screened with the first mixture of molecules, by incubating the beads with 4 μg of biotinylated serum in 1 ml of PBSTGNaN$_3$ for one hour. The beads were then washed three times in PBSTGNaN$_3$ to remove unbound or loosely associated proteins. The beads were then incubated for one hour with 1 μl streptavidin-alkaline phosphatase conjugate in 1 ml PBSTGNaN$_3$. Following the streptavidin-alkaline phosphatase conjugate (1.5 mg/ml) incubation, the beads were washed two times in TBS and once in alkaline phosphatase buffer (100 mM Tris-HCl pH 8.8, 100 mM NaCl, and 2.34 mM MgCl$_2$) to remove unbound streptavidin-alkaline phosphatase conjugate and to replace the phosphate-based buffer with a Tris-based buffer.

The first marking step was performed by incubating the beads with a solution of BCIP at a final concentration of 0.165 mg/ml in one ml of alkaline phosphatase buffer. After incubation for one hour, beads with bound protein were stained varying shades of blue through the action of the attached streptavidin-alkaline phosphatase conjugate. The BCIP reaction was terminated by washing three times with PBSTGNaN$_3$ to remove unreacted BCIP.

After screening with the serum and the first marking step, the beads were screened with the target mixture by incubating the beads with 4 μg of biotinylated plasma in 1 ml of PBSTGNaN$_3$ for one hour. The beads were then washed three times in PBSTGNaN$_3$ to remove unbound or loosely associated proteins. The beads were incubated a second time, as above, for one hour with streptavidin-alkaline phosphatase conjugate and then washed two times in TBS and once in alkaline phosphatase buffer.

After washing, approximately 2,500 red reference beads were added to serve as reference points in subsequent steps.

Next, the beads were immobilized in a support matrix. A solution of 1% low-melt SeaPlaque agarose in 5 ml of alkaline phosphatase buffer was prepared. The agarose solution was cooled to about 45° C., and successive 1 ml aliquots were added to the column, withdrawn with beads, and placed in the lid of a sterile polystyrene OmniTray. The dimensions of the lid were 86 mm wide×128 mm long×5 mm high. The bead-agarose solution was spread evenly across the surface of the lid through a gentle shaking action before being allowed to cool and harden. After the bead-agarose solution had hardened, 5 ml of alkaline phosphatase buffer was added to the lid and allowed to equilibrate for five minutes. During this time, the agarose pulled slightly away from the edge of the lid. After five minutes, the alkaline phosphatase buffer was removed with gentle suction, and the lid was placed on a flatbed scanner set up for transparency scanning.

The second marking step was begun. Five ml of alkaline phosphatase buffer containing 0.165 mg/ml BCIP was gently added drop-wise on top of the agarose in the lid. Then the lid and beads were immediately scanned at 1200 dpi with no sharpening or color adjustments using the transparency scanning mode. The resultant RGB image was saved and designated image "A." The second marking step was completed by incubating the beads for one hour. Then, the beads were scanned again and the second scanned image designated image "B." Images "A" and "B" were compared, and if needed, the beads were scanned again after one more hour. After scanning, the BCIP reaction was stopped by the addition of 10-20 drops of 1 N HCl and gentle rocking of the lid to mix the acid with the alkaline phosphatase buffer. The addition of acid lowers the pH below the optimum for alkaline phosphatase and essentially stops the reaction. Scanned plates were stored covered, in a humid environment, until needed. When necessary, distilled water was added drop-wise to prevent agarose dehydration.

Image and Data Analysis. Proper analysis of images "A" and "B" required that the images be of the same size and that all common points in the two images be aligned so that they could be precisely overlaid. This image manipulation was accomplished with Adobe Photoshop. After alignment, the images were converted to grayscale and saved in raw image format. The RGB image can either be converted directly to a grayscale image or the red channel in a RGB image can be used if increased sensitivity is needed.

Data analysis of the image pairs was accomplished using custom programming, done in C code. The C program created three arrays. The size of each of the arrays, in bytes, was determined by multiplying the height of the image by the width. Images "A" and "B" were then loaded into the first two arrays, and the formula $(B-A)/A$ was applied to each pair of corresponding points. Division-by-zero errors were avoided by adding one where necessary. The numerical results of $(B-A)/A$ were placed in the third array at the same relative point in the array at which the "A" and "B" values were resident. Following these calculations, the values in the third array were written out in raw data image format.

The contents of the third data file were opened as a raw image file, designated image "C." Image "C" was used as a template to identify the true positive beads, those that bound molecules essentially unique to the plasma. This was accomplished by a visual analysis of all points corresponding to a particular bead in image "C," as well as images "A" and "B." Beads that appeared whole in image "C" were confirmed as unique to image "B" by side-by-side comparison of images "A" and "B." Arrows pointing towards beads of interest were drawn on image "C." These arrows were then overlaid on image "B"; the combined image was printed and used as a picking template for retrieval of the beads of interest. To isolate beads of interest, the lid containing the beads immobilized in agarose was placed on top of the picking template and then both were placed under a dissecting microscope. Gel-loading pipette tips were used to retrieve those beads indicated by arrows.

Determination of primary amino acid sequence. After retrieval, beads of interest were washed sequentially in distilled water, 8M guanidine-HCl, 8M guanidine-HCl, and distilled water prior to submission for automated peptide sequencing. The following ligands were identified: cHTLHQc, cFHNNHc, cAHVWHc, cHVHPWc, cHYHVSc, cHGHTIc, cMHGHFc, cYGHFSc, cNLTHIc, cHYQTGc, cGIHYLc, and cPFHHSc, where each amino acid is an L-amino acid.

The invention has been described above with reference to the preferred embodiments. Those skilled in the art may envision other embodiments and variations of the invention that fall within the scope of the claims.

We claim:

1. A method for determining the differences between the molecular interactions of two different mixtures of molecules, comprising:
    labeling a first mixture of molecules and a target mixture of molecules;
    introducing said first mixture of molecules to a combinatorial library of solid phase supports;
    incubating said combinatorial library with said first mixture of molecules;
    performing a first marking step to mark those of said solid phase supports that have a molecule of said first mixture bound to them;
    introducing said target mixture of molecules to said combinatorial library;
    incubating said combinatorial library with said target mixture of molecules;
    obtaining a first image showing as marked those of said solid phase supports that have a molecule of said first mixture bound to them;
    performing a second marking step to mark those of said solid phase supports that have a molecule of said target mixture bound to them;
    obtaining a second image showing as marked those of said solid phase supports that have a molecule of said target mixture bound to them; and
    creating a third image identifying those of said solid phase supports that have a molecule of said target mixture bound to them, wherein said third image is created by comparing said first image and said second image;
    wherein said first and said second images are graphical images, and said third image is created by comparing said first and said second images on a pixel-by-pixel basis; and, further, wherein said first image is image "A," said second image is image "B," and said third image is created by applying a formula (B−A)/A on a pixel-by-pixel basis.

2. A method for determining the differences between the molecular interactions of two different mixtures of molecules and identifying a ligand specific for a molecule in one of the mixtures, comprising:
    labeling a first mixture of molecules and a target mixture of molecules;
    introducing said first mixture of molecules to a combinatorial library of solid phase supports;
    incubating said combinatorial library with said first mixture of molecules;
    performing a first marking step to mark those of said solid phase supports that have a molecule of said first mixture bound to them;
    introducing said target mixture of molecules to said combinatorial library;
    incubating said combinatorial library with said target mixture of molecules;
    obtaining a first image showing as marked those of said solid phase supports that have a molecule of said first mixture bound to them;
    performing a second marking step to mark those of said solid phase supports that have a molecule of said target mixture bound to them;
    obtaining a second image showing as marked those of said solid phase supports that have a molecule of said target mixture bound to them;
    creating a third image identifying those of said solid phase supports that have a molecule of said target mixture bound to them, wherein said third image is created by comparing said first image and said second image;
    isolating one of said solid phase supports identified in said third image; and
    determining the chemical structure of a ligand on one of said isolated solid phase supports;
    wherein said first and said second images are graphical images, and said third image is created by comparing said first and said second images on a pixel-by-pixel basis; and, further, wherein said first image is image "A," said second image is image "B," and said third image is created by applying a formula (B−A)/A on a pixel-by-pixel basis.

* * * * *